(12) United States Patent
Müller et al.

(10) Patent No.: US 9,707,326 B2
(45) Date of Patent: Jul. 18, 2017

(54) MOBILE SYSTEM FOR SEPARATING DONOR BLOOD BY MEANS OF GRAVITATIONAL FORCE

(71) Applicant: 3M Innovative Properties Company, St. Paul, MN (US)

(72) Inventors: Roland Müller, Zug (CH); Bodo Von Harten, Wuppertal (DE)

(73) Assignee: 3M Innovative Properties Company, St. Paul, MN (US)

( * ) Notice: Subject to any disclaimer, the term of this patent is extended or adjusted under 35 U.S.C. 154(b) by 281 days.

(21) Appl. No.: 14/417,429

(22) PCT Filed: Jul. 18, 2013

(86) PCT No.: PCT/EP2013/065208
§ 371 (c)(1),
(2) Date: Jan. 26, 2015

(87) PCT Pub. No.: WO2014/016198
PCT Pub. Date: Jan. 30, 2014

(65) Prior Publication Data
US 2015/0209494 A1 Jul. 30, 2015

(30) Foreign Application Priority Data
Jul. 25, 2012 (EP) .................................. 12177871

(51) Int. Cl.
*A61M 1/02* (2006.01)
*A61M 1/34* (2006.01)
*B01D 63/02* (2006.01)

(52) U.S. Cl.
CPC ........ *A61M 1/0209* (2013.01); *A61M 1/0218* (2014.02); *A61M 1/0272* (2013.01);
(Continued)

(58) Field of Classification Search
None
See application file for complete search history.

(56) References Cited

U.S. PATENT DOCUMENTS

2006/0011545 A1 1/2006 Latza
2010/0084331 A1 4/2010 Heuser
(Continued)

FOREIGN PATENT DOCUMENTS

DE 295 16 471 U1 1/1996
DE 10 2010 030238 A1 12/2011
(Continued)

OTHER PUBLICATIONS

Oct. 15, 2013 International Search Report issued in International Application No. PCT/EP2013/065208.

*Primary Examiner* — Chester Barry
(74) *Attorney, Agent, or Firm* — Scott A. Baum

(57) ABSTRACT

A mobile system for separating donor blood by gravitational force into erythrocyte concentrate and plasma. The system includes a first bag serving as a reservoir for the blood to be separated and at least a second and third bag for respectively receiving the erythrocyte concentrate and plasma, and also multiple tubes for connecting the flexible bags to a separator module having a separating membrane in the form of a bundle of hollow fibers. This system is divided into at least one first and one second sterilely packaged, individual subsystem. The first subsystem includes the individual bags and associated connection tubes and the second subsystem includes the separator module, and male/female connectors.

13 Claims, 3 Drawing Sheets

(52) U.S. Cl.
 CPC ............ *A61M 1/3496* (2013.01); *B01D 63/02* (2013.01); *B01D 2319/04* (2013.01)

(56) References Cited

U.S. PATENT DOCUMENTS

2010/0137826 A1    6/2010  Watts et al.
2013/0323711 A1*  12/2013  Singh .................. G01N 33/491
                                                                                    435/2

FOREIGN PATENT DOCUMENTS

| EP | 2 277 573 A1 | 1/2011 |
| JP | 2001-198214 | 7/2001 |
| WO | WO 2004/050145 | 6/2004 |
| WO | 2007/012321 A2 | 2/2007 |
| WO | 2008/070220 A1 | 6/2008 |
| WO | 2008/083965 A2 | 7/2008 |
| WO | 2008/142694 | 11/2008 |
| WO | 2011/157822 A1 | 12/2011 |

* cited by examiner

MOBILE SYSTEM FOR SEPARATING DONOR BLOOD BY MEANS OF GRAVITATIONAL FORCE

BACKGROUND

The invention relates to a mobile system for separating donor blood by means of gravitational force into erythrocyte concentrate and plasma, having a first bag serving as a reservoir for the blood to be separated and at least a second and third bag for respectively receiving erythrocyte concentrate and plasma, and also multiple tubes for connecting the flexible bags consisting of plastic material to a separator module having a separating membrane in the form of a bundle of hollow fibers.

The separation of blood is carried out using centrifugation in the method used as a rule for separating donor blood into erythrocyte concentrate and plasma. A four-bag system is commonly used thereby, wherein the bags are sterilely connected via tubing. The first bag, filled with whole blood in the course of a donation, is connected via a leukocyte filter to the second bag for receiving filtered whole blood. When this second bag is filled with filtered blood, it is deaerated and heat-sealed.

The centrifugation is carried out in a rotator, wherein rotational speed, centrifugation time, and temperature are determined by the blood components to be separated and the bag system used. The centrifuged whole blood is introduced into a separator, which detects the separation layer between plasma and cells using optical detectors, for example, and then presses them out into the respective connected bags.

Although this is a proven standard method for preparing blood components, it also has several disadvantages.

Since electrical power is inevitably required to perform the centrifugation and separation, this standard method for preparing blood components can only be carried out in the presence of a corresponding power source.

In addition to the high acquisition and maintenance costs which are connected with this known system, it is disadvantageous that the functional implementation of the blood separation can only be carried out by trained personnel. Furthermore, due to the high rotational speed, red blood cells can burst upon impact with the walls of the centrifuge, and their contents can be discharged to the surrounding plasma. As these red blood cells can also contain poisonous substances and pathogens, in addition to hemoglobin and cell fragments, these dangerous contents must be extracted prior to further processing of the plasma, which causes additional work and costs.

It is also disadvantageous that preparation of stored blood, carried out in correspondingly equipped, central facilities, is often associated with a time delay if the blood donation is carried out in mobile donation stations and the donations must be transported over long distances to the corresponding center before the fractionation into blood components can be carried out there.

A mobile system for separating donor blood by means of gravitational force into erythrocyte concentrate and plasma of the type described at the beginning is known under the designation "ErySep Classic" from Lmb Technologie GmbH. This known system, independent of an external power source, has the fundamental advantage that it enables the separation of donor blood without the necessity of conventional logistics because it requires no electricity or electrical devices such as centrifuges, plasma extractors, and the like.

In the case of this known system, the different necessary bags are connected to the separator module via tubes, which are permanently joined to the connectors of the separator module, in particular glued or heat-sealed, so that this complete system must be sterilized as a unit. If the mandatory test of the donor blood from the pre-donation bag indicates that the donor blood is unusable, the complete system consisting of bags, connecting tubes, and separator module becomes unusable and, accordingly, the complete unit, intended for single use, must be disposed of.

SUMMARY

It is the object of the present invention to achieve a substantial improvement in the previously known system for separating donor blood by means of gravitational force into erythrocyte concentrate and plasma, namely in an economic respect and also with regard to the quality of the blood components obtained and the desired high hematocrit level.

This object is substantially achieved according to the invention in that the system is divided into at least one first and one second sterilely packaged, individual subsystem, that the at least one first subsystem comprises the individual bags and the associated connecting tubes and the second subsystem comprises the separator module, and that male/female connectors, in particular Luer-lock connectors, are provided for connecting the tubes to the separator module, one part of said connectors being fixed or integrated in the housing of the separator module and the complementary part of said connectors being connected to the end of the respective tube.

By this means, for example, a two-in-one filtration and separation system is provided for single use, which enables in an especially economical way a reliable separation of the blood components, wherein there is no need for electricity or electronic devices, and also no need for specially trained personnel, and the separated components are available for immediate use.

By dividing the complete system into at least two defined subsystems, not only are important handling advantages achieved in practice, but also, in the case of unusable donor blood, only the inexpensive at least one first subsystem must be disposed of and not the complete system. This economically significant effect has special importance when high proportions of contaminated blood must be taken into consideration, e.g. in malarial regions.

A further advantage of the division is that the second subsystem, i.e. the separator module, can be combined with different embodiments of the at least one first subsystem. For example, a leukocyte filter between the primary bag for donor blood and the separator module is not necessary for all applications and for all regions in the world. By dividing the complete system into at least two defined subsystems, the second subsystem with the separator module can then be selectively combined with first subsystems which contain a leukocyte filer, or with first subsystems without a leukocyte filter. In this way, the economics of the complete system can be increased.

The basic concept of the division of the complete system according to the invention enables, in an advantageous way, the sterilization of the packaged subsystems using different methods, wherein steam sterilization, proven in practice, can be used for the at least one first subsystem, and the second subsystem with the separator module can for example be sterilized using gamma or beta radiation. This procedure leads to maximum reliability with regard to the demands for the sterility of the complete system. Also contributing to this is that the open gender connectors in the sterilely packaged subsystems are closed off by removable fitting caps so that the assembly of the subsystems into a complete system can be carried out in a way long proven in medical technology, and thereby sterile or at least virtually sterile connections can be guaranteed.

The present mobile system for separating donor blood by means of gravitational force into erythrocyte concentrate and plasma is divided into at least one first and one second sterilely packaged subsystem. The second subsystem comprises the separator module. The individual bags and associated connection tubes are comprised by the at least one first subsystem. The individual bags and connection tubes and also further required or optional components of the mobile system, with the exception of the separator module, can be comprised by a single first subsystem. However, multiple first subsystems can also be present, into which the individual bags and connecting tubes, as well as further required or optional components of the mobile system, are divided. In one embodiment, the mobile system for separating donor blood by means of gravitational force can have two first subsystems, wherein one of these subsystems comprises the first bag serving as a reservoir for the blood to be separated, i.e. the primary bag for donor blood, possibly an pre-donation bag for test purposes, a donor cannula, and the associated connection tubes. The additional first subsystem can then comprise the second and third bags for receiving the erythrocyte concentrate and plasma, respectively, and also the connecting tubes associated therewith. A division into three or more first subsystems is also possible, which then enables a further allocation of the components of the complete system into subgroups.

An embodiment is preferred, however, in which the mobile system for separating donor blood by means of gravitational force is divided into a single first and a second sterilely packaged, individual subsystem, and that the single first subsystem comprises the entirety of the individual bags and associated connection tubes. An embodiment of this type offers advantages with regard to the handling of the individual subsystems and for their assembly.

In particular, in the previously cited embodiment, the connections for the inlet and outlet tubes of the bags in the sterilely packaged first subsystem are joined using a Y connector via male/female connections, so that the steam sterilization of this subsystem can be carried out with the bags connected to one another. If the two subsystems are assembled into a complete system, the connections to the Y connector are separated and the required male/female connections are established.

According to an especially advantageous embodiment of the invention, a U-shaped bundle of membrane hollow fibers is provided in the tubular-shaped housing of the separator module, which housing tapers slightly toward the bottom, wherein the housing of the separator module has a bottom outlet fitting for the plasma and on the cover-end an inlet fitting connected to the inlets of the hollow fiber bundle for the donor blood to be separated and also an outlet fitting for the erythrocyte concentrate. It is thereby of particular importance, with respect to manufacturing and the desired high functional reliability, that the gender connectors necessary for the sterile or at least virtually sterile tube connections are fixed directly in the respective fittings, in particular by gluing or heat-sealing, or these gender connectors are preferably cast directly on the fittings by using a specific mold shape and are thus integral components of the fittings, wherein in the latter case a separate handling of the connectors and the step of gluing or heat-sealing can be omitted.

For the required correct connection of the respective tubes via the connectors, it is preferred if the bottom outlet fitting of the separator module has a different gender connector than the cover-end fittings. In one embodiment, it is advantageous if the bottom outlet fitting of the separator module has a male connector, and the cover-end fittings have female connectors, which can be coupled on the one hand to a male connector of the tube leading to the donor bag and on the other hand to a male connector of the tube leading to the bag for the erythrocyte concentrate. Correspondingly, the tube leading to the bag for plasma has a female connector and thus can be coupled to the male connector of the bottom outlet fitting of the separator module. According to a further embodiment, it is advantageous that the bottom outlet fitting of the separator module has a female connector, which can be coupled to a male connector of the tube leading to the plasma bag. The cover-end fittings of the separator module in this embodiment have male connectors, which can be coupled on the one hand to a female connector of the tube leading to the donor bag and on the other hand to a female connector of the tube leading to the erythrocyte concentrate bag.

In a further advantageous embodiment, a pressure adapter can be or is coupled to the cover-end fitting for coupling the bag for the erythrocyte concentrate, to which pressure adapter in turn the tube leading to the bag for the erythrocyte concentrate can be coupled.

The special pressure adapter, with gender connectors provided on both ends, can be a component of the sterilely packaged second subsystem. An embodiment is advantageous in which the special pressure adapter, with gender connectors provided on both ends, is a component of the sterilely packaged at least one first subsystem. This enables the provision of mobile systems for separating donor blood by means of gravitational force in which the second subsystem is always implemented in the same way, and is coupled as required to first subsystems, which according to need can comprise a pressure adapter and/or also e.g. a leukocyte filter downstream of the primary bag for donor blood.

The pressure adapter can be a line section that has a reduced inside diameter in comparison to the rest of the connection tubes, wherein this inside diameter is selected in connection with the length of this line section such that, as a result of the increased pressure drop during use, an especially high hematocrit level is obtained in the erythrocyte concentrate. The pressure adapter can be a correspondingly configured line section in the form of a separate tube section, a rigid tube, or a capillary. In addition, the pressure adapter can be a line section provided with an adjustable valve. Embodiments are also possible as are described as pressure adjustment devices in WO 2011/157822, to which reference is explicitly made to its disclosure in this regard.

In an advantageous embodiment, the tube section between the primary bag for donor blood and the gender connector for coupling with the cover-end inlet fitting of the separator module or, in the presence of a leukocyte filter between the primary bag and separator module, the tube section between the leukocyte filter and the gender connector for coupling with the cover-end inlet fitting of the separator module is designed with respect to its inside diameter and length such that the pressure drop through this tube section during use is high enough to prevent an excessively rapid flow of the blood into the separator module and thus hemolysis of the blood. By this means, a simplification is achieved in the handling of the complete system during use, for example, also in that an otherwise conventional roller clamp for adjusting the volume flow can be omitted.

Further advantageous features and characteristics of the invention are described in the dependent claims and are also addressed by means of the subsequently explained sample embodiment.

BRIEF DESCRIPTION OF THE DRAWINGS

The sample embodiment will be explained by means of the drawings. The drawings are as follows.

Figure 1:
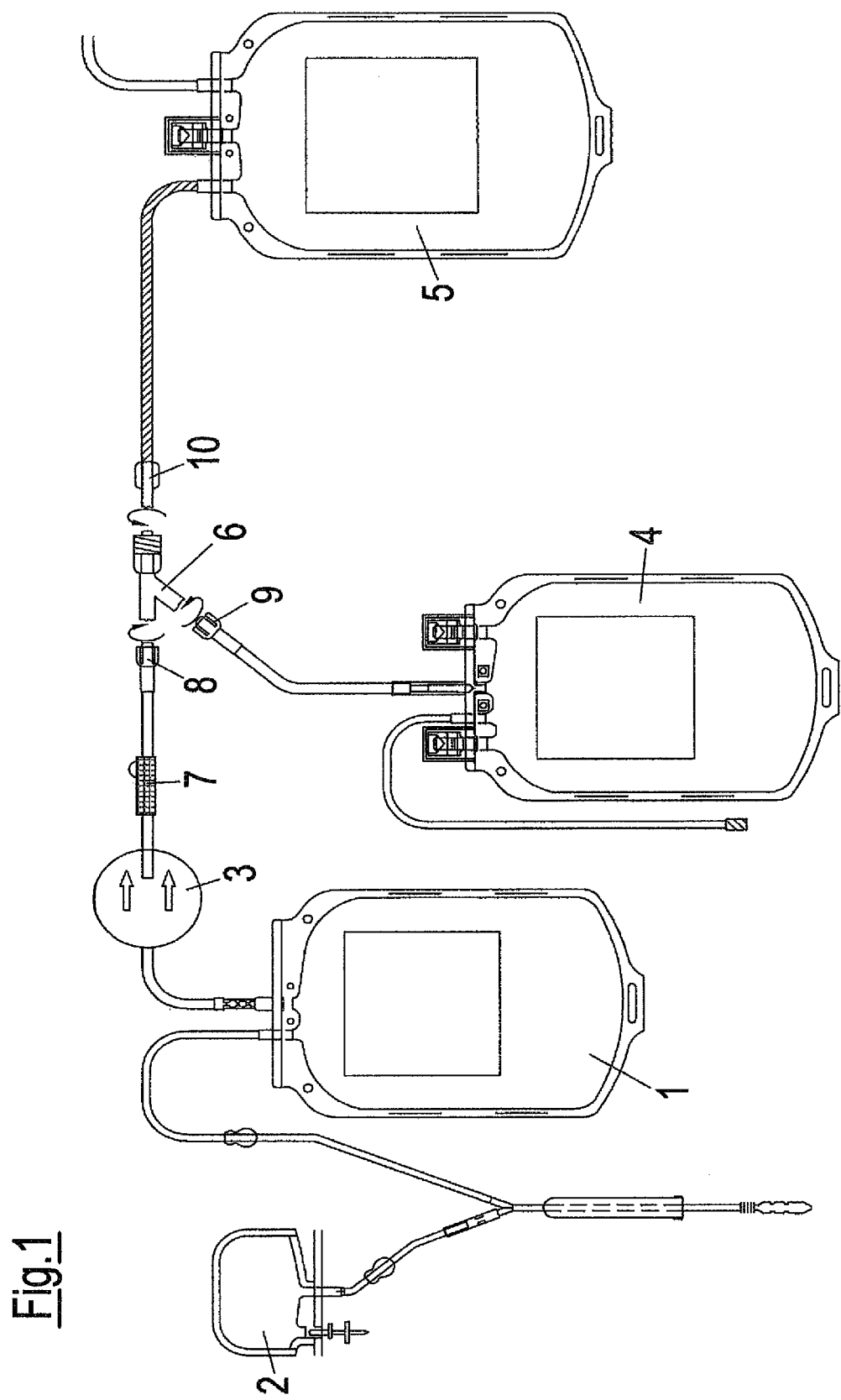
FIG. 1 is a representation of an embodiment of a single first subsystem.

The schematic representation according to FIG. 1 shows the components of the first subsystem, which are to be sterilely packaged. This first subsystem accordingly comprises a first bag 1 for the donor blood, a second bag 4 for the erythrocyte concentrate obtained in the course of the blood separation, and also a third bag 5 for the plasma obtained during the blood separation. These bags are conventional, flexible bags made of transparent plastic material, which are provided in turn in the conventional way with inlet and outlet tubes and breaker valves, as is also the case for other blood donor systems.

An pre-donation bag 2 intended for test purposes, and likewise a conventional donor cannula, are associated in the conventional way with the first bag 1 intended for receiving donor blood.

In the present case, a conventional leukocyte filter 3, followed by a roller clamp 7, is connected in the outlet line of the first bag 1. As stated, the presence of a leukocyte filter in the outlet line is optional and is not required in every case. A male connector 8 is connected to the end of the outlet tube and coupled to one branch of a Y connector 6 within the context of the first subsystem. The adjacent branch of the Y connector 6 is joined to a male connector 9 at the end of the connection tube for the erythrocyte container 4. A connector provided on the free end of the connection tube to the plasma bag 5 is implemented as a female connector 10 and is coupled with the remaining third connection of the Y connector 6.

The first subsystem, assembled in the way described, consisting of bags connected to each other via tubes, can be made germ-free in a conventional way using steam sterilization in the packaged state, so that this first subsystem is available in the form of an economic, sterilely packaged unit for practical use for blood collection. In the conventional way, directly after completion of a blood donation, the inlet tube to the donor blood bag 1 is sealed air tight, which can be carried out by heat sealing or by clamping off the tube using a metal clamp.

As stated, the previously listed components of the first subsystem can also be divided for example into two first subsystems. In this case, the first bag 1 for the donor blood, the pre-donation bag 2 intended for test purposes, the donor cannula, the leukocyte filter 3, the roller clamp 7, and the associated inlet and outlet tubes can be contained in a first subsystem. The second bag 4 for the erythrocyte concentrate obtained within the course of blood separation and also the third bag 5 for the plasma obtained during the blood separation, together with the associated inlet and outlet tubes and breaker valves, can be components of the additional first subsystem. In this case, a simple connection of the bags 4, 5 via the male connector 8 and the female connector 10 is sufficient and a connection via a Y connector 6 is not required.

Figure 2:
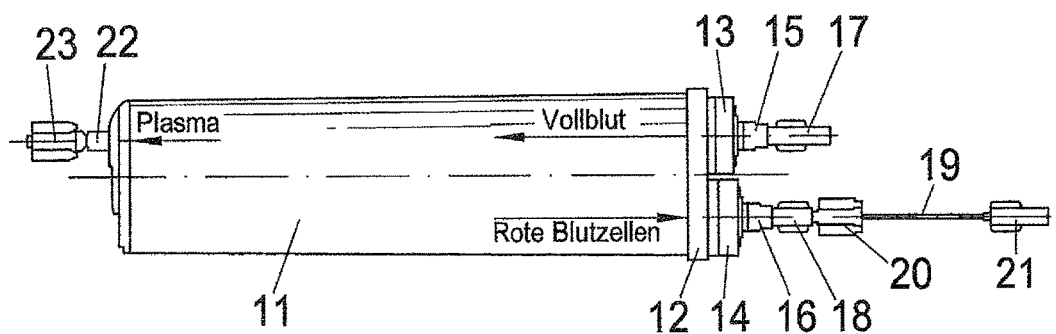
FIG. 2 is a representation of an embodiment of the second subsystem.

FIG. 2 shows, in the form of an outside view, a separator module 11, in the housing of which a bundle comprising a plurality of membrane hollow fibers is arranged. This bundle can extend in the longitudinal direction through the housing; however, the hollow fiber bundle is preferably arranged in a U-shape in the housing, as shown in the embodiment here, so that the inlet and outlet ends of the fiber bundle are at one end of the housing.

The transparent housing, preferably made of polycarbonate, has on the bottom a discharge fitting 22 for the plasma obtained within the course of the separation process, and a gender connector, for example a male connector 23, is integrated, glued, or fused in this discharge fitting 22. The gender connector is preferably an integral component of the discharge fitting 22, for example by producing it together with the discharge fitting 22 in an injection molding process.

On the opposite end of the separator module 11, the housing is terminated by a support cap 12, wherein the ends of the membrane hollow fibers are fixed in this support cap or in a corresponding end plate, so that the whole blood can flow into the interior of the hollow fibers via a flow convergence cap 13, and the retentate containing the red blood cells, after the separation from the plasma penetrating the hollow fiber walls, can be discharged into the outlet fitting 16 in the flow convergence cap 14.

The flow convergence caps 13, 14 are respectively equipped with an inlet fitting 15 or an outlet fitting 16, into which gender connectors in the form of female connectors 17, 18 are directly inserted and sealed leaktight with these fittings by gluing or heat sealing, analogous to the discharge fitting 22 for the plasma. It is also preferred here that these gender connectors are connected integrally to the inlet fitting 15 or the outlet fitting 16.

The special pressure adapter, present in an advantageous embodiment and represented as a component of the second subsystem, comprises a pressure-resistant tube 19 and gender connectors 20, 21 on the ends thereof. This pressure adapter is intended for connecting the separator module 11 to the tube leading to the erythrocyte container 4.

The inside diameter of this tube section 19 is less than the inside diameter of the other connection tubes. The inside diameter of this tube section 19, in general of the line section used as the pressure adapter, is preferably in the range from approximately 0.5 to 3.5 mm, while the length thereof is approximately 40 mm to 150 mm. Due to the special pressure adapter, here implemented as a tube or line section 19, a pressure increase is effected in the discharge line to the erythrocyte container 4, which results in an increased filtrate flow of the plasma through the pores of the hollow fiber membranes. As a result of this, less residual plasma enters the erythrocyte bag. By this means, the proportion of the liquid in the total volume of the erythrocyte bag is reduced, which results in a significant increase in the hematocrit level.

The direct integration of the gender connectors into the connection fittings of the separator module 11, and the resulting absence of otherwise required connection tubes on the ends of the separator module, significantly facilitate and simplify performing the obligatory leakage tests in series production.

The second subsystem presented here, consisting of the separator module 11 and the associated pressure adapter 19, 20, 21, is preferably not steam sterilized, but instead subjected to a sterilization via gamma radiation or beta radiation, since in this way the required sterility of the entire structure of the separator module, consisting of a plurality of components, and the special pressure adapter can be ensured.

It should also be noted that, due to the selected dimensioning of the pressure adapter, here the tube section 19, an increase of the hematocrit level in the erythrocyte concentrate of approximately 10 percentage points compared to the initial hematocrit level in the donor blood can be reliably achieved, for example from 42% to 52%.

The open gender connectors 17, 21, 23 in the second subsystem are closed off using removable end caps. As the known Luer-lock connectors are preferably used as connectors in the complete system, the closure of the gender connectors is carried out using suitable, preferably colored, caps in the Luer-lock procedure.

Figure 3:
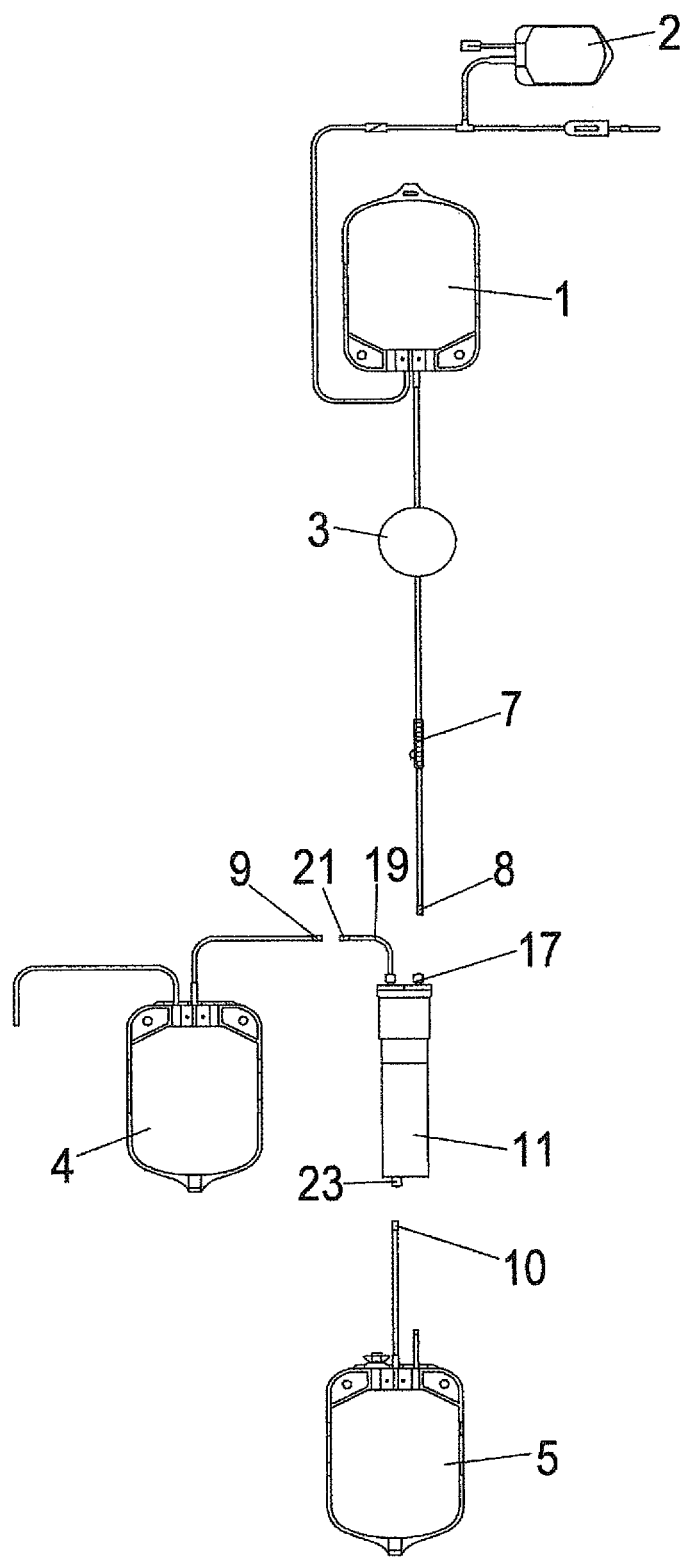
FIG. 3 is a schematic representation of the complete system consisting of the first and second subsystems in an arrangement characteristic for blood separation, as can be realized for example by hanging the different components on a conventional stand.

FIG. 3 shows the assembly of the two subsystems into the complete system, wherein the representation was selected to illustrate the basic positioning of the individual components vertically over each other, as is necessary for the gravitational force operation to take effect within the course of the blood separation. As a rule, the corresponding components are hung for this purpose on a suitable stand.

The first bag 1 containing the donor blood is at the highest point, the outlet of which is provided with a breaker valve as usual. In this representation, the pre-donation bag 2 with connection tube and receiving cannula is also shown here.

Below the container 1, in the case shown, a conventional leukocyte filter 3 and a subsequent roller clamp 7 are provided in the tubing line functioning as the blood delivery tube. At the end of this blood delivery tube, the male connector 8, separated from the Y connector 6 of the first subsystem, is coupled to the female connector 17 of the separator module 11, forming a sterile or virtually sterile connection.

A further sterile or virtually sterile connection is established between the female connector 21 at the end of the tube section 19 and the male connector 9 at the end of the tube leading to the second bag 4 for the erythrocyte concentrate. In addition, the male connector 23 provided on the bottom of the separator module 11 is joined to the female connector provided at the free end of the connection tube to the plasma container 5, at which point the complete system is in a fully-functional, i.e. finished state.

It must be noted that the assembly of the first and second subsystems is naturally only carried out if the test performed in the course of a blood donation, using the blood located in the pre-donation bag 2, indicates that the blood donation is untainted. If this is not the case, only the first subsystem must be disposed of; the more complex and expensive second subsystem is not affected and can be used for the next blood separation to be carried out. Using the system according to the invention, which is easily manageable without problems even by persons who are not specially trained, each unit of donor blood can be separated into a unit of erythrocyte concentrate and a unit of plasma, wherein both components are ready for immediate use, wherever and whenever they are needed.

LIST OF REFERENCE NUMBERS

1 First bag or primary bag for donor blood
2 Pre-donation bag for test purposes
3 Leukocyte filter
4 Second bag for the erythrocyte concentrate
5 Third bag for plasma
6 Y connector
7 Roller clamp
8 Male connector
9 Male connector
10 Female connector
11 Separator module
12 Support cap
13 Flow convergence cap
14 Flow convergence cap
15 Inlet fitting
16 Outlet fitting
17 Female connector
18 Female connector
19 Tube section
20 Male connector
21 Female connector
22 Discharge fitting
23 Male connector

The invention claimed is:

1. A mobile system for separating donor blood by means of gravitational force into erythrocyte concentrate and plasma comprising:
 a first bag serving as a reservoir for the blood to be separated
 at least a second bag and a third bag for respectively receiving erythrocyte concentrate and plasma, and
 multiple tubes for connecting the first bag, the second bag, and the third bag to a separator module having a separating membrane in the form of a bundle of hollow fibers,
 wherein
 the mobile system is divided into at least one first and one second sterilely packaged individual subsystems,
 the at least one first subsystem comprises the first bag, the second bag, and the third bag and the multiple tubes, and
 the second subsystem comprises the separator module and male/female connectors provided for connecting the multiple tubes to the separator module, one part of said connectors being fixed or integrated in a housing of the separator module; and
 wherein a complementary part of said connectors being connected to the end of the respective tube in the first subsystem.

2. The mobile system according to claim 1, wherein the first and the second sterilely packaged individual subsystems are sterilized by means of different methods.

3. The mobile system according to claim 1, wherein
 the male/female connectors comprise open gender connectors in the first and the second sterilely packaged individual subsystems, and the open gender connectors are closed off by removable fitting caps.

4. The mobile system according to claim 1, wherein
 the first subsystem comprises two first subsystems wherein one of these subsystems comprises the first bag, an optional pre-donation bag, a donor cannula, and associated connection tubes; and the additional first subsystem comprises the second bag, the third bag, and the associated connection tubes.

5. The mobile system according to claim 1, wherein
 in the sterilely packaged first subsystem, the connectors of the inlet and outlet tubes of the first bag, the second bag, and the third bag are joined using a Y connector via male/female connections.

6. The mobile system according to claim 1, wherein the at least one sterilely packaged first subsystem comprises a leukocyte filter in an outlet line of the first bag, a downstream, adjustable clamping device located after the leukocyte filter, as well as a pre-donation bag and a donor cannula.

7. The mobile system according to claim 1, wherein the sterilely packaged second subsystem comprises a pressure adapter provided on both ends with a connector, the pressure adapter coupled to a complementary connector of the separator module associated with an erythrocyte outlet.

8. The mobile system according to claim 1, wherein the at least one sterilely packaged first subsystem comprises a pressure adapter provided on both ends with a connector, the pressure adapter configured to couple with a complementary connector of the separator module associated with an erythrocyte outlet.

9. The mobile system according to claim 7, wherein the pressure adapter is a line section with an inside diameter in the range from approximately 0.5 to 3.5 mm and a length in the range from approximately 40 mm to 150 mm.

10. The mobile system according to claim 1, wherein the housing of the separator module is tubular-shaped and has on a bottom a discharge fitting for the plasma and on a cover end an inlet fitting for the donor blood to be separated and an outlet fitting for the erythrocyte concentrate.

11. The mobile system according to claim 10, wherein the gender connectors required for the sterile tube connections are fixed to the housing by gluing them to or casting them in or on the housing.

12. The mobile system according to claim 10, wherein the bottom discharge fitting of the separator module has a different gender connector than the cover-end inlet and outlet fittings.

13. The mobile system according to claim 1, wherein Luer connectors are used as connectors and gender connectors are closed off with caps.

* * * * *